Figure 1:
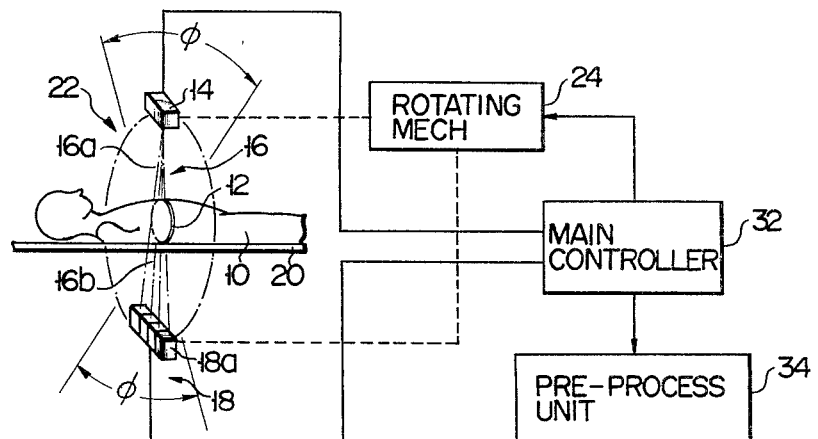

United States Patent [19]

Inouye et al.

[11] 4,205,375

[45] May 27, 1980

[54] METHOD AND APPARATUS FOR PERFORMING COMPUTED TOMOGRAPHY

[75] Inventors: Tamon Inouye, Tokyo; Hiroyuki Mizutani, Kawasaki, both of Japan

[73] Assignee: Tokyo Shibaura Electric Co., Ltd., Japan

[21] Appl. No.: 874,065

[22] Filed: Jan. 31, 1978

[30] Foreign Application Priority Data

Jan. 31, 1977 [JP] Japan ................................. 52-8703

[51] Int. Cl.$^2$ ........................................... G01N 23/00
[52] U.S. Cl. ................................ 364/414; 250/445 T
[58] Field of Search .................... 364/414; 250/363 S, 250/445 T

[56] References Cited

U.S. PATENT DOCUMENTS

| | | | |
|---|---|---|---|
| 3,778,614 | 12/1973 | Hounsfield | 250/363 S |
| 3,878,373 | 4/1975 | Blum | 364/414 |
| 3,983,399 | 9/1976 | Cox, Jr. et al. | 364/414 |
| 4,048,503 | 9/1977 | Taylor | 250/445 T |
| 4,052,620 | 10/1977 | Brunnett | 250/445 T |
| 4,071,760 | 1/1978 | LeMay | 250/363 S |
| 4,081,681 | 3/1978 | Froggatt | 250/445 T |

OTHER PUBLICATIONS

Kay et el., "Radionuclide Tomographic Image Reconstruction Using Fourier Transform Techniques", *Journal of Nuclear Medicine*, Nov. 1974, vol. 15, No. 11, pp. 981-986.

G. N. Ramachandran, "Reconstruction of Substance from Shadow", Indian Academy of Sciences, vol. LXXIV, No. 1, Section A (1971).

G. N. Ramachandran, "Three-Dimensional Reconstruction from Radiographs and Electron Micrographs: Application of Convolutions Instead of Fourier Transforms", Proc. Nat. Acad. Sci., vol. 68, No. 9, pp. 2236-2240, Sep. 1971.

*Primary Examiner*—Errol A. Krass
*Attorney, Agent, or Firm*—Finnegan, Henderson, Farabow, Garrett & Dunner

[57] ABSTRACT

In a method and an apparatus for performing computed tomography using radiation, the apparatus includes a data selecting unit which divides into a plurality of groups and stores the projection data signals provided by a multitude of radiation beams being projected along several different directions through a slice to be imaged in a subject and penetrating the slice from the external circumference of it with each of the groups corresponding to the beams penetrating along selected directions within a specific scan sector less than 180°; a Fourier transform unit for calculating sample values for the one-dimensional Fourier transform of a projection function formed by each group of said projection data signals; a function calculating unit for calculating sample values for the one-dimensional Fourier transforms as mentioned above for a plurality of projecting directions selected outside said specific scan sector; and a reconstruction unit for calculating the absorption coefficient distribution of the radiation beams in said slice from both said sets of sample values, and a display unit.

4 Claims, 6 Drawing Figures

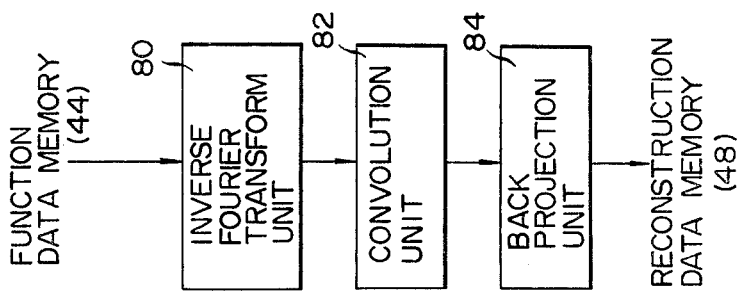
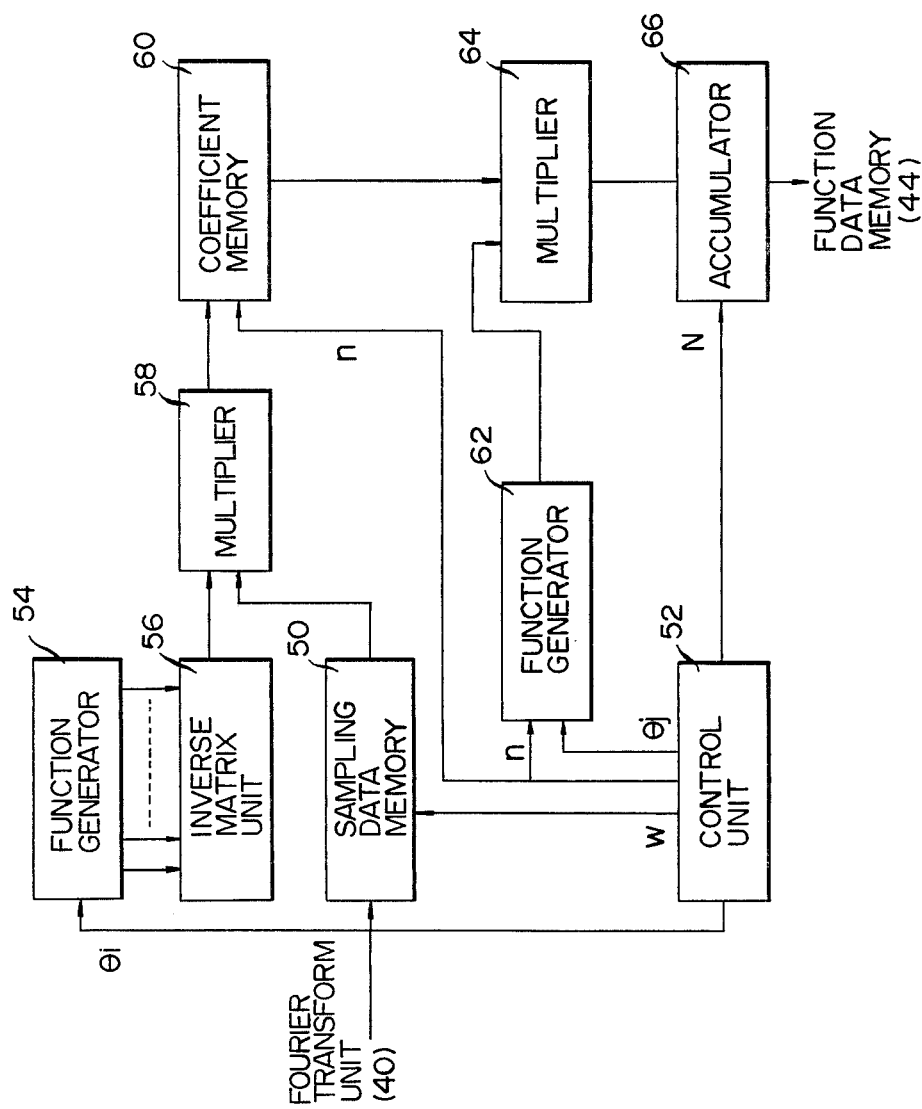

METHOD AND APPARATUS FOR PERFORMING COMPUTED TOMOGRAPHY

This invention relates to a method and an apparatus for performing computed tomography using radiation, said apparatus comprises a scanning means to project a multitude of radiation beams into a slice in a foreground subject to be imaged from the external circumference around said slice in various different directions which are flush with said slice; and detecting means to generate electric signals indicating the intensities of said radiation beams having penetrated through said slice; a pre-processing unit to send out projection data signals corresponding to said radiation beams upon receipt of said electric signals; a display unit to display an image of said slice in accordance with a distribution of radiation beam absorption coefficients, said distribution is calculated on the basis of the projection data signals sent from said pre-processing unit.

Apparatus of this kind is generally known as a computed tomography apparatus or system. In one typical example radiation beams are projected into a slice defined across a subject. Radiation beams are projected from a multitude of different angular directions and penetrate the slice in parallel with both flat surfaces of the slice. The intensities of the beams are measured before and after penetrating the slice, and radiation beam absorption coefficients in various parts of the slice are calculated from the data obtained via said measurements, and an image of the slice is reconstructed on the basis of the distribution of said absorption coefficients, and displayed on a display unit.

For reconstructing the image in the above described form of computed tomography system, various methods have been suggested in which representative ones are the Convolution method, the Filtered Back Projection method and the Fourier Transformation method. To be effective, however, these methods require that the subject be located at the center of a rotating scanner having a radiation source and radiation detectors mounted thereon, because each method uses the projection data obtained by radiation beams projected to the subject at various specified angles about the circumference of the slice. Therefore, these conventional apparatus have disadvantages such as requiring a bulky and complicated structure permitting the subject to be positioned within a central bore accurately, subjecting the subject, e.g. a patient, to serious discomfort by having him received into the narrow cavity, and requiring a long time for reconstruction of the image due to the fact that the projection data signals are obtained from the whole circumference. As the result, the anxiety and the discomfort of the patient and the radiation dose projected to the patient are increased.

The object of this invention is to provide a computed tomography apparatus using radiation which is free from the disadvantages described heretobefore, and which is compact and capable of collecting the projection data and forming the displayed image in a short time.

In order to realize the object mentioned above, an apparatus for performing computed tomography using radiation comprises a projection data sorting unit to divide into groups the projection data signals for each unit of beams parallel respectively with a plurality of specified directions selected from within a first range of angles less than 180° and to store a plurality of said groups of projection data signals thus obtained; a Fourier transform unit receiving said groups of projection data signals to calculate sample values, with respect to the projection angles, of a one-dimensional Fourier transform of a projection function formed of said projection data signal groups; a function calculating unit to calculate, based upon said sample values, the sample values with respect to the projection angles of the one-dimensional Fourier transform of a projection function formed of projection data signals corresponding to a plurality of specified projecting directions selected from a range of angles outside said first range of angles, i.e. a second range of angles; and a reconstruction unit to calculate the distribution of radiation beam absorption coefficients in said slice on the basis of both of said sample values.

The method and the apparatus of this invention for performing computed tomography using radiation have advantages in that since they are capable of calculating for a full 360° scan based projection data on a first range of angles less than 180°, the angle by which the radiation source and the radiation detectors rotate may be substantially reduced hence the apparatus may be of compact construction and collection of the necessary data for reconstruction and displaying the image can be accomplished in a short time, so that the apparatus is free from the above mentioned disadvantages inherent in present conventional apparatus.

Figure 4:
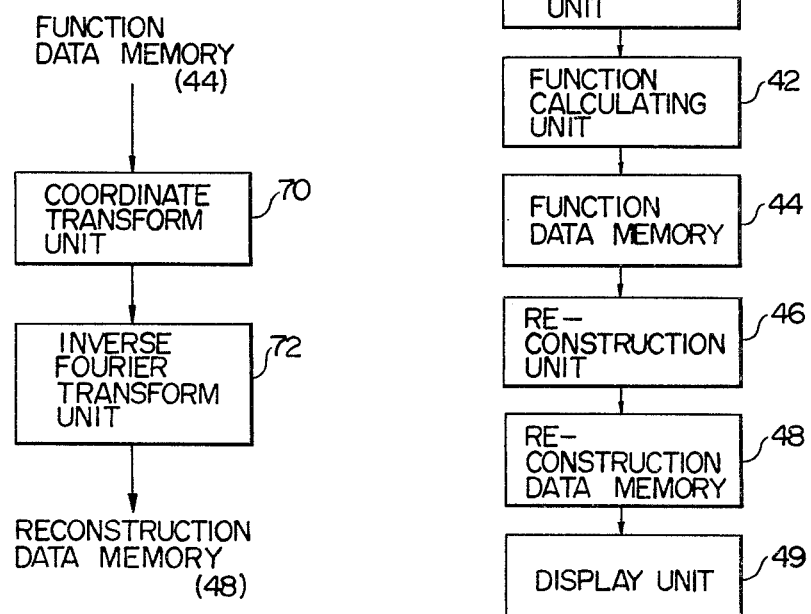
Figure 2:
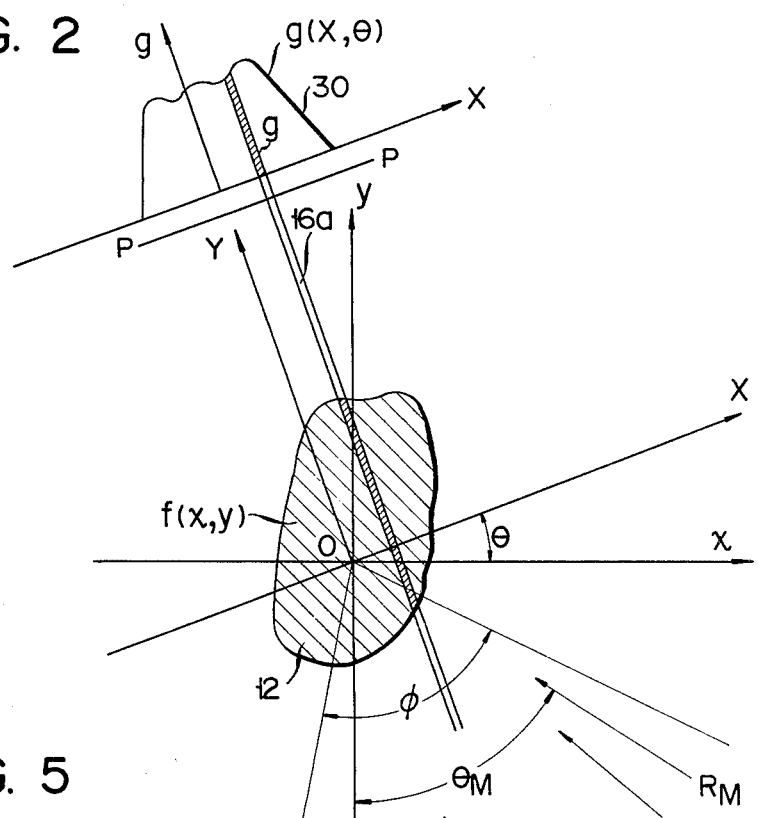
Figure 5:
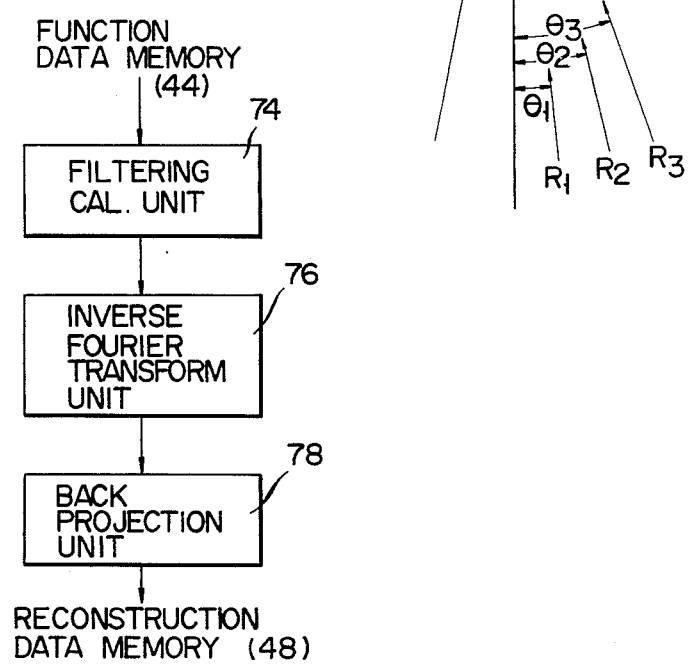

This invention can be more fully understood from the following detailed description when taken in conjunction with the accompanying drawings, in which:

FIG. 1 is a schematic illustration including a block diagram showing one embodiment of the present invention;

FIG. 2 schematically illustrates the method of the reconstructing an image of the slice from the projection data in accordance with the present invention;

FIG. 3 is a block diagram showing the detailed structure of the function calculating unit of the present invention; and FIGS. 4, 5, 6 are block diagrams showing three different embodiments of the reconstructing unit of the image present invention.

In FIG. 1, radiation beams 16 generated from a radiation source 14 such as an X-ray source or a Gamma ray source are irradiated to a slice 12 defined along a plane across a subject, e.g. a patient 10, and then detected by detector 18. In this embodiment, the radiation beams 16 take the form of a fan.

The beams having penetrated through the slice 12, i.e., the penetration beams, attenuate due to being absorbed in the slice 12, and the intensities of these penetration beams are detected by the detector 18. The subject, i.e. the patient 10, is positioned on a suitable support bed 20 and scanned with the radiation beams 16 from the radiation source 14 which rotates around the subject, being driven by a scanner 22. The scanner 22 includes the radiation source 14, the detector 18, a frame (not shown) supporting both of them and a rotating mechanism 24 which is capable of rotating the frame around the patient through an angle $\phi$ as shown, so that the radiation beams 16 may be projected through the slice 12 from various directions within the angle $\phi$ with respect to the slice 12, i.e. a first range of angles. This angle $\phi$ is selected to be less than 180°. The penetration beams make angles between themselves and will reach the detectors 18 in a diverging state. The detector 18 comprises a plurality of detector elements 18a arrayed so as to detect the intensity of each of these diverging beams. To this end, these detector elements 18a are arranged in side-by-side relation so that they each detect a different one of the diverging penetration beams.

In FIG. 2, 12 designates the slice which is positioned in parallel with the surface of the paper of the drawing. Taking a point 0 defined in the slice as the point of origin, a rectangular coordinate system (x,y) and an another rectangular coordinate system (X,Y) displaced counterclockwise through an angle $\theta$ from the former system are shown. One beam 16a projected from the radiation source (not shown) follows a path parallel to the Y-axis. This beam 16a is attenuated an amount corresponding to the intergral value of the radiation absorption coefficients of all material lying along the path through which this beam has penetrated and then is projected onto a detector (not shown) positioned in a plane perpendicular to the surface of the paper and having the cross section designated by the line P—P perpendicular to the Y-axis. The output electrical signals from the detector are converted into projection data $g_0$. The plane on which the detector is positioned is called the $\theta$-projection plane. On coordinate system (X,g) depicted at the top of the + side of the Y-axis, the projection data $g_0$ is plotted as a function of the penetrating direction $\theta$ and distances X from the point of origin 0.

In FIG. 2, numerous beams (not shown) are projected to the surface of the slice 12 in parallel with the beam 16a, so that projection data for the various values of X may be obtained. These projection data may be plotted on the aforesaid coordinate system (X,g). In FIG. 2, however, each of the individual data points is not shown but their maximum values are connected to show an envelope. This envelope will be hereinafter called the projection function. The multitudinous projection data which constitute the projection function $g(X,\theta)$ shown at 30, i.e. the projection profile, are obtained by selecting measurements for beams aligned in parallel with the Y-axis from the projection data measured at all predetermined rotating angles for the numerous diverging beams shown in FIG. 1 and FIG. 2 as said beams rotate through the angle $\phi$. A plurality of projection functions $g(X,\theta)$ for various values of $\theta$ are obtained in the same manner. The multitudinous projection data for all projection angles are divided by their projection directions into groups and stored in a memory. For the sake of clarity these data are indicated graphically in FIG. 2.

The f(x,y) shown in FIG. 2 indicates the radiation absorption coefficients of the points having a coordinate values (x,y). The variables x and y represent the absorption coefficient distribution for the area 12, i.e. the reconstructed image of the slice under examination. While, the $g(X,\theta)$, as clear from the above explanation, indicates the projection data when a beam spaced by a distance X from the point of origin 0 is projected onto the $\theta$-projection plane, and if X is considered to be a variable with $\theta$ being constant, it describes the projection profile 30. A projection function 30 may be obtained for the projection beams having respectively different M directions which are designated by arrows $R_1, R_2, \ldots R_M$ making angles $\theta_1, \theta_2, \ldots \theta_M$ respectively with the Y-axis. When the beams are projected within the range of angles $\theta_1 \sim \theta_M$, the X-axis and the Y-axis are rotated by angles $\theta_1, \theta_2, \ldots \theta_M$ respectively in a counterclockwise direction with respect to the x-axis and the y-axis.

Now returning to FIG. 1, a main controller 32 controls the rotational movement of the scanner 22, the operations of both the radiation source 14 and the detector 18 and receives the electrical signals from the detector 18 and transfers them to a pre-processing unit 34.

The pre-processing unit 34 converts the electrical signals into digital projection data and outputs them. A projection data memory 36 stores projection data.

A data selecting unit 38 divides the projection data stored in the projection data memory 36 according to each of the beams being parallel with M different directions $R_1, R_2, \ldots R_M$ defined with the first range of angle $\phi$ ($\phi$ is less than 180°) in FIG. 2 into groups and transfers them to the next stage.

A Fourier transform unit 40 receives sequentially M groups of the projection data having been divided by the data selecting unit 38 and calculates the one-dimensional Fourier transform of these data according to the following equation:

$$G(\omega,\theta) = \int_{-\infty}^{+\infty} g(X,\theta) e^{-i\omega X} dX \qquad (1)$$

in the above equation, i indicates a imaginary unit, $\omega$ is an angular frequency which is generally used in the calculation of Fourier transforms about space. Here, however, what are obtained actually are the sample values $G(\omega,\theta)$ calculated with respect to each of the angles $\theta_1, \theta_2, \ldots \theta_M$.

It should be noted that the projection functions $G(\omega,\theta)$ measured according to the present invention are limited to those corresponding to the directions defined within the sector $\phi$. This is for the reason that in the present invention for the reconstruction of the slice image the theorem saying "The one-dimensional Fourier transform of the projection function $g(X,\theta)$ of a certain reconstruction image f(x,y) is equal to the central section, i.e. the section containing the point of origin provided by cutting at a corresponding angle the two-dimensional Fourier transform of that image f(x,y)" is applied. This is explained mathematically as follows.

First, the two-dimensional Fourier transform $F(\xi,\eta)$ of the reconstruction image f(x,y) to be displayed is set up according to the equation $$F(\xi,\eta) = \int_{-\infty}^{\infty} \int_{-\infty}^{\infty} f(x,y) e^{-i(\xi x + \eta y)} dx dy \qquad (2)$$

where $\xi$ and $\eta$ are spatial frequencies used in the calculation the Fourier transform for the x direction and the y direction respectively. Then, $\xi$ and $\eta$ in equation (2) are substituted by the relations:

$$\xi = \omega \cos\theta, \quad \eta = \omega \sin\theta \qquad (3)$$

transforming equation (2) into polar coordinate form as follows:

$$F(\omega,\theta).$$

The aforesaid theorem states:

$$G(\omega,\theta) = F(\omega,\theta) \ldots \qquad (4).$$

According to the method and apparatus of the present invention for reconstructing the slice image, a calculation is applied to $F(\xi,\eta)$ to obtain the Inverse Fourier transformation according to equation (5) which is transformed, by substitution of the relation (3) to the function $F(\omega,\theta)$, i.e. $G(\omega,\theta)$, so as to calculate the absorption coefficients on the x-axis. This operation is executed sequentially about a plurality of directions defined on the whole circumference around the slice to obtain numerous absorption coefficients covering subsequently all portions of the slice. This requires the one-dimensional Fourier transform $G(\omega,\theta)$ covering the whole circumference.

$$f(x,y) = \frac{1}{4\pi^2} \int_{-\infty}^{\infty} \int_{-\infty}^{\infty} F(\xi,\eta)e^{i(\xi x + \eta y)} d\xi d\eta \quad (5).$$

That is, to utilize the above theorem, the projection functions $G(\omega,\theta)$ for the whole circumference around the slice 12 are required. Notwithstanding, in the present invention, since the projection functions only within the actually measured first range of angles $\phi$ are measured, a method is utilized to derive $G(\omega,\theta)$ for the range outside of the sector $\phi$, i.e. the calculable angle range or the second range of angles, from the values of $G(\omega,\theta)$ obtained within the sector $\phi$, for which a function calculating unit 42 described hereafter is used.

Conventional systems have various disadvantages because they measure $G(\omega,\theta)$ over the whole circumference by rotating the radiation source 14 and the detector 18 around the slice 12 by 360°

The function calculating unit 42 calculates the $G(\omega,\theta)$ functions which fall in the calculable or second range as mentioned above. The principle of calculating is as follows. The $g(X,\theta)$ function shown in FIG. 2 is a value corresponding to the intensity of the penetration beam 16a which is defined by an angle of $\theta$ corresponding to the penetrating direction of the radiation beam and the position X of said beam 16a. The $g(X,\theta)$ function is a real function. Accordingly, the real part $ReG(\omega,\theta)$ and the imaginary part $ImG(\omega,\theta)$ of the function $G(\omega,\theta)$ obtained by applying the one-dimensional transformation to said $g(X,\theta)$ are represented by the following expressions, respectively.

$$ReG(\omega,\theta) = \int_{-\infty}^{\infty} g(x,\theta) \cos\omega X dX$$

$$ImG(\omega,\theta) = \int_{-\infty}^{\infty} g(x,\theta) \sin\omega X dX$$

Namely, the $ReG(\omega,\theta)$ and $ImG(\omega,\theta)$ are even and odd functions with respect to $\omega$, respectively.

Next, the function $G(\omega,\theta+\pi)$ must be considered. The points $(\omega,\theta+\pi)$ and $(\omega,\theta)$ are located in positions symmetrical about the point of origin. Therefore, the position of the point $(\omega,\theta+\pi)$ is the same as that of the point $(-\omega,\theta)$, so that $G(\omega,\theta+\pi)$ is the same as $G(-\omega,\theta)$. Accordingly, $$ReG(\omega,\theta+\pi) = ReG(-\omega,\theta) = ReG(\omega,\theta)$$

$$ImG(\omega,\theta+\pi) = ImG(-\omega,\theta) = -ImG(\omega,\theta)$$

The above results show the following. The value of $ReG(\omega,\theta)$ exhibits a cosine change when the $\theta$ value is varied keeping $\omega$ fixed but this change is repeated at a cycle of $\pi$ or 180°. On the other hand, value of the $ImG(\omega,\theta)$ exhibits a sine change when the $\theta$ value is varied keeping $\omega$ fixed but this change is a cyclical one whereby as the sign $+$ of the $ImG(\omega,\theta)$ value changes to $-$ or vice versa for each variation of $\pi$ angle, the $ImG(\omega,\theta)$ value returns to the original.

In conclusion, the $ReG(\omega,\theta)$ and $ImG(\omega,\theta)$, accordingly $G(\omega,\theta)$, can both be said to be a function which varies in a cycle of 360° with respect to $\theta$.

From such periodicity, it will be understood that the real part $ReG(\omega,\theta)$ and the imaginary part $ImG(\omega,\theta)$ may be developed in Fourier series with respect to $\theta$ for various values of $\omega$, which is shown in the following equations:

$$ReG(\omega,\theta) = \sum_{n=0}^{\infty} [A_n(\omega)\cos 2n\theta + B_n(\omega)\sin 2n\theta]$$

$$ImG(\omega,\theta) = \sum_{n=0}^{\infty} [C_n(\omega)\cos(2n+1)\theta + D_n(\omega)\sin(2n+1)\theta]$$

This series, however, consists of terms which are ordered to approach zero, hence, the terms from the first to the appropriate order may be employed exclusive of other less significant higher terms. The number of terms from the first term of this series which are utilized and summed will be determined so that the reconstructed and displayed image of the slice obtained by using the values of the shortened series is substantially the same as the image obtained by summing all of the terms the series.

Now the real part $ReG(\omega,\theta)$ and the imaginary part $ImG(\omega,\theta)$ of the calculation for obtaining the Fourier transform really employed is as follows:

$$ReG(\omega,\theta) \approx \sum_{n=0}^{N} [A_n(\omega)\cos 2n\theta + B_n(\omega)\sin 2n\theta] \quad (6)$$

$$ImG(\omega,\theta) \approx \sum_{n=0}^{N} [C_n(\omega)\cos(2n+1)\theta + D_n(\omega)\sin(2n+1)\theta]$$

In order to substitute into equation (6) the $\theta$ of the aforesaid calculable range of angles to and calculate $ReG(\omega,\theta)$ and $ImG(\omega,\theta)$ corresponding to this range, $A_n(\omega)$, $B_n(\omega)$, $C_n(\omega)$ and $D_n(\omega)$ should be obtained from measurement.

The series $ReG(\omega,\theta)$ contains $A_n(\omega)$ and $B_n(\omega)$, each containing $(N+1)$ coefficients, therefore the series $ReG(\omega,\theta)$ includes $2(N+1)$ coefficients in total. Similarly, the series $ImG(\omega,\theta)$ contains $(N+1)$ coefficients $C_n(\omega)$ and $D_n(\omega)$ respectively with $2(N+1)$ in total. Accordingly, taking M, i.e. the number of projection directions of the beams defined within the aforesaid actually measured range of angles $\phi$, as at least $2(N+1)$, the Fourier transformations $G(\omega,\theta_1)$, $G(\omega,\theta_2)$, ... $G(\omega,\theta_{2(N+1)})$ for $g(X,\theta_1)$, $g(X,\theta_2)$, ... $g(X,\theta_{2(N+1)})$ are obtained. The above equation (6) will be substituted by the real parts $ReG(\omega,\theta_1)$, $ReG(\omega,\theta_2)$, ... $ReG(\omega,\theta_{2(N+1)})$ and the imaginary parts $ImG(\omega,\theta_1)$, $ImG(\omega,\theta_2)$, ... $ImG(\omega,\theta_{(N+1)})$ corresponding to the angles $\theta_1, \theta_2, \ldots \theta_{2(N+1)}$ so as to set up at least $2(N+1)$ equations for the real parts and for the imaginary parts respectively. Then, from these equations, all values of $A_n(\omega)$, $B_n(\omega)$, $C_n(\omega)$ and $D_n(\omega)$ can be calculated.

If all of the coefficients have been calculated as described, $\theta$ within the equation (6) can be substituted by the values for $\theta$ selected within the aforesaid calculable or second range of angles, whereby it is possible to calculate the $ReG(\omega,\theta)$ and $ImG(\omega,\theta)$ and then the Fourier transforms for the projection angles of the beams within said second range.

Thus, by means of actual measurements and calculations, the numerous Fourier transforms $G(\omega,\theta)$ selected within the desired 360° range can be obtained.

FIG. 3 is a block diagram showing one example of the detailed structure of the function calculating unit 42 hereinbefore described. Two sets of the structures shown in FIG. 3 are provided in this apparatus. One of the units receives the real part $ReG_1(\omega,\theta)$ of the Fourier transform $G_1(\omega,\theta)$ due to actual measurements from the Fourier transform unit 40 and outputs to function data memory 44 the $ReG_2(\omega,\theta)$ values calculated in this unit 42 for the second range of angles together with the $ReG_1(\omega,\theta)$ values derived from actual measurements for the first range of angles $\phi$. On the second hand, the other unit 42 calculates the imaginary part $ImG_2(\omega,\theta)$ of the Fourier transform $G_2(\omega,\theta)$ for the calculable or second range of angle on the basis of the imaginary part $ImG_1(\omega,\theta)$ values derived from actual measurements received from the Fourier transform unit 40 and outputs to the function data memory 44 the imaginary part $ImG_1(\omega,\theta)$ values derived from actual measurements together with the imaginary part $ImG_2(\omega,\theta)$ values calculated in this unit 42.

Referring to the block diagram of FIG. 3, the circuit is hereinafter described and its operation explained for the case of calculating the real part $ReG(\omega,\theta)$ values for the calculable or second range of angles. As the calculation of the imaginary part $ImG(\omega,\theta)$ values proceeds in the same manner as that for the real part values, an explanation of it will be omitted. Each real part function $ReG_1(\omega,\theta)$ of the Fourier transform $G_1(\omega,\theta)$ supplied from the Fourier transform unit 40 is stored in a sampling data memory 50. A control unit 52 supplies angle data $\theta_i (i=1, 2, \ldots M)$ within the actually measured sector $\phi$ to a function generator 54, whereupon the function generator 54 supplies the values of $\cos 2n\theta_i$ and $\sin 2\theta_i$ to an inverse matrix unit 56. The inverse matrix unit 56 is arranged depending on the coefficients $2(N+1)$ of the equations with respect to the real part in the equation (6) and calculates the inverse matrix of the matrix by which are multiplied the coefficients $A_0(\omega)$, $A_1(\omega), \ldots A_N(\omega)$ and $B_0(\omega), B_1(\omega), \ldots B_N(\omega)$ so as to calculate the above mentioned real values $ReG(\omega,\theta_1)$, $ReG(\omega,\theta_2), \ldots ReG(\omega,\theta_M)$. That is, the unit 56, on the basis of the results supplied with $\cos 2\theta_i$ and $\sin 2\theta_i$, provides the value of the inverse matrix to a multiplier 58. The multiplier 58 is supplied with the real part values $ReG(\omega,\theta)$ from the sampling data memory 50 on the basis of the values of $\omega$ being supplied from the control unit 52 and with the values of the inverse matrix calculated as described above, and then calculates the coefficients $A_n(\omega)$ and $B_n(\omega)$, the resulting values of which are stored in a coefficient memory 60.

The control unit 52 supplies the angle data $\theta_j$ describing the calculable or second range of angles to a function generator 62 and also sequentially supplies parameters n to the function generator 62 and the coefficient memory 60. A multiplier 64 multiplies the coefficients $A_n(\omega)$ and $B_n(\omega)$ being outputted from the coefficient memory 60 by $\cos 2n\theta_j$ being outputted from the function generator 62 respectively and applies the results to an accumulator 66. The accumulator 66 adds these values $A_n(\omega)\cdot\cos 2n\theta_j$ and $B_n(\omega)\cdot\sin 2\theta_j$ respectively in the order of n to calculate $$\sum_{n=0}^{N} A_n(\omega) \cdot \cos 2n\theta_j$$

and $$\sum_{n=0}^{N} B_n(\omega) \cdot \sin 2n\theta_j$$

and, when n reaches N, sums the two totals and then applies the result to the function data memory 44. Then the control unit 52 sends a different value of $\omega$, whereupon the same operation is repeated and the values of the real part function $ReG(\omega, \theta)$ of the Fourier transforms $G(\omega, \theta)$ are stored sequentially in the function data memory 44.

Similarly the values of the imaginary part functions $ImG(\omega, \theta)$ of the Fourier transforms $G(\omega, \theta)$ are calculated and stored in the function data memory 44. Thus, all of the values of the Fourier transforms $G(\omega, \theta)$ which are necessary to reconstruct the absorption coefficient distribution in all portions of the slice are stored in the memory 44.

The values of $G(\omega, \theta)$ which have been stored in the memory 44 are supplied to a reconstruction unit 46. The unit 46 obtains the absorption coefficients of the individual points within the slice of the subject from the values of $G(\omega, \theta)$ and supplies these coefficients to a reconstruction data memory 48.

FIGS. 4, 5, 6 show the structure and operations of three kinds of the systems which may be used for the reconstruction unit 46. FIG. 4 implements the Fourier transformation method, FIG. 5 the Filtered Back Projection method, and FIG. 6 the Convolution Integral method respectively. In FIG. 4, the numerous transforms of $G(\omega, \theta)$ supplied from the function data memory 44 are transformed from polar coordinate form $(\omega, \theta)$ into rectangular coordinate form $(\xi, \eta)$ by a coordinate transformation unit 70 operating in accordance with the interpolation method. These Fourier transforms which have been converted to the rectangular coordinate system are equal to the components having the same direction of the two-dimensional Fourier transform $F(\xi, \eta)$ of the absorption coefficient distribution $f(x,y)$ in the silce 12, and a multitude of radial cross sections which are obtained across the original point of the spatial frequency distribution surface of the image of the slice. Consequently the Fourier transform of the image of the slice is obtained in polar coordinate form. Accordingly this function $F(\xi, \eta)$ is transformed into the two-dimensional inverse Fourier transform by an inverse Fourier transform unit 72, and is obtained. The $f(x,y)$ values are supplied to the reconstruction data memory 48 and stored therein.

In FIG. 5, the Fourier transform values $G(\omega, \theta)$ from the function data memory 44 are supplied to a filtering calculation unit 74 to be multiplied with a filter function and then the unit 74 calculates a one-dimensional inverse Fourier transform by means of an inverse Fourier transform unit 76. Thus, modified projection data are provided. Then, back projection using the modified projection data is carried out by a back projection unit 78. The absorption coefficient distribution $f(x,y)$ obtained by the above calculations is sent to and stored in the reconstruction data memory 48 in FIG. 1.

In FIG. 6, the Fourier transform values $G(\omega, \theta)$ supplied from the function data memory 44 are processed to obtain one-dimensional inverse Fourier transform values by an inverse Fourier transform unit 80 so as to provide the projection data for a plurality of the directions selected over the whole circumference. Then, convolution integraion of the projection data, with modified function sharpening of the image, is executed by a convolution unit 82, so as to enhance the sharpness of the image, and the result of the execution is back-projected by a back projection unit 84. Thus, the absorption coefficient distribution f(x,y) with respect to all portions of the slice is obtained. The data for the function f(x,y) are stored in the reconstruction data memory 48.

Accordingly, the f(x,y) data stored in the reconstruction data memory 48 are displayed visually by the display unit 49 shown in FIG. 1, so that the desired tomographic image of the slice is provided for diagnostic purposes.

As hereinbefore described, in the present invention, the projection data obtained by actual measurement over the scan sector $\phi$ is sufficient to derive the absorption coefficient distribution for the whole slice so that the image of the slice may be reconstructed and displayed. Therefore, with the apparatus of this invention, it is possible to make the scanner 22 (FIG. 1) simple and compact. Thus, it will be appreciated that the apparatus of the present invention not only is mechanically simpler and more compact but also reduces both the mental and the physical discomfort of the patient, eliminating the need for placing the patient in a narrow cavity and permitting the operator of the apparatus to adjust the position of the patient more easily. It has the further advantage in that since the projection data pickup is done only within a scan angle of less than 180°, the time requires for displaying the image of the slice is shortened and this leads to a decrease in the radiation dose applied to the patient. From a medical point of view, the apparatus of the invention has a further remarkable advantage in that it is effective for diagnosing cases wherein it is impossible to collect projection data along the whole circumference around the slice.

The embodiment described above is only an example conveniently applied to ordinary use but, not limited to this, various modifications may be considered.

For example, a supersonic wave source as well as an X-ray source or a gamma-ray source may be utilized to supply the projection energy.

Further, in the above embodiment, radiation beams distributed in the form of a fan are employed but beams projected in parallel with one another may be also used. In the latter case, the data selection unit 38 of FIG. 1 may be omitted. Also, the function unit 42 of FIG. 1 may be arranged so as not to execute the calculation employing the inverse matrix as shown in FIG. 3 but to use, for example, a deduction method according to the method of least squares. Further, these processes may be executed by means of a digital computer. In the above embodiment, the range $\phi$ within which the projection data are measured has been explained as a continuous range. However, the range of angles within which the actual measurements are performed may be divided into a plurality of discrete ranges and, with the projection data derived from these ranges, the succeeding executions carried out in the manner described.

What we claim is:

1. In a computed tomography system, the method for generating an image of an internal area under examination comprising the steps of:
   (a) projecting a plurality of radiation beams through said area and detecting the beams penetrating said area to generate projection data signals representing the intensities of said detected beams;
   (b) repeating step (a) for a plurality of different scan angles $\theta$ located in a scan sector of less than 180° centered about a point in said area;
   (c) dividing the projection data signals generated in steps (a) and (b) into groups wherein each said group includes data signals generated at a common scan angle;
   (d) calculating the one-dimensional Fourier transform for each group of said data signals to derive sample values $G_1(\omega,\theta)$ for each of said groups, where $\omega$ is a predetermined Fourier angular frequency;
   (e) calculating the real and imaginary part Fourier transform coefficients $A_n(\omega)$, $B_n(\omega)$, $C_n(\omega)$, and $D_n(\omega)$ according to the equations:

$$ReG(\omega,\theta) = \sum_{n=0}^{N} [A_n(\omega)\text{Cos}2n\theta + B_n(\omega)\text{Sin}2n\theta]$$

$$ImG(\omega,\theta) = \sum_{n=0}^{N} [C_n(\omega)\text{Cos}(2n+1)\theta + D_n(\omega)\text{Sin}(2n+1)\theta]$$

by substituting into said equations the real and imaginary part sample values corresponding to the $G_1(\omega,\theta)$ values obtained in step (d) and the values of the scan angles $\theta$ within said scan sector and solving the multiple equations so constructed for $A_n(\omega)$, $B_n(\omega)$, $C_n(\omega)$ and $D_n(\omega)$;
   (f) utilizing the equations of step (e) with the calculated values of said Fourier transform coefficients and values of scan angles $\theta$ outside of said scan sector to calculate a plurality of one-dimensional Fourier transform sample values $G_2(\omega,\theta)$ for scan angles $\theta$ outside of said scan sector;
   (g) determining absorption coefficient values for a plurality of points within said internal area under examination based on said Fourier transform sample values $G_1(\omega,\theta)$ and $G_2(\omega,\theta)$; and
   (h) displaying said absorption coefficient values in a two-dimensional plot to construct an image of said internal area.

2. The method set forth in claim 1 wherein step (g) comprises the steps of:
   (i) transforming said sample values $G_1(\omega,\theta)$ and $G_2(\omega,\theta)$ from polar coordinate form to rectangular coordinate form $F(\xi,\eta)$ by coordinate interpolation; and
   (ii) converting said $F(\xi,\eta)$ values by two-dimensional inverse Fourier transformation into coordinate values f(x,y) representing absorption coefficient values for points within said internal area.

3. The method set forth in claim 1 wherein step (g) comprises the steps of:
   (i) multiplying said $G_1(\omega,\theta)$ and $G_2(\omega,\theta)$ values by filter function values to obtain modified Fourier transform values;
   (ii) calculating the one-dimensional inverse Fourier transform for said modified Fourier transform values to obtain modified projection data signal values for a plurality of scan projection angles $\theta$; and
   (iii) back-projecting said modified projection data signal values for a plurality of points f(x,y) within said internal area to obtain said absorption coefficient values.

4. The method set forth in claim 1 wherein step (g) comprises the steps of:

(i) calculating the one-dimensional inverse Fourier transform for said $G_1(\omega,\theta)$ and $G_2(\omega,\theta)$ values to obtain projection data signal values for a plurality of scan angles inside and outside of said scan sector;

(ii) performing convolution integration of said projection data signal values with a convolution function to obtain modified projection data signal values for said plurality of scan angles; and (iii) back-projecting said modified projection data signal values for a plurality of points $f(x,y)$ within said internal area to obtain said absorption coefficient values.

* * * * *